(12) United States Patent
Luan et al.

(10) Patent No.: US 9,146,211 B1
(45) Date of Patent: Sep. 29, 2015

(54) NANO-RING GATE ELECTRODE NANOCHANNELS

(71) Applicant: International Business Machines Corporation, Armonk, NY (US)

(72) Inventors: Binquan Luan, Chappaqua, NY (US); Sung-wook Nam, Croton-on-Hudson, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 14/225,694

(22) Filed: Mar. 26, 2014

(51) Int. Cl.
C12Q 1/68 (2006.01)
G01N 27/414 (2006.01)
G01N 27/447 (2006.01)

(52) U.S. Cl.
CPC .......... *G01N 27/4145* (2013.01); *C12Q 1/6869* (2013.01); *G01N 27/44791* (2013.01)

(58) Field of Classification Search
CPC ........................... C12Q 1/68; C12Q 2565/631
USPC ........................................ 977/704, 880, 883
See application file for complete search history.

(56) References Cited

U.S. PATENT DOCUMENTS

| | | | |
|---|---|---|---|
| 7,312,155 B2 | 12/2007 | Dubin et al. | |
| 7,670,770 B2 | 3/2010 | Chou et al. | |
| 7,898,005 B2 | 3/2011 | Yang et al. | |
| 8,105,471 B1 | 1/2012 | Han et al. | |
| 8,273,532 B2 | 9/2012 | Gershow et al. | |
| 8,384,195 B2 | 2/2013 | Wang et al. | |
| 2007/0122313 A1* | 5/2007 | Li et al. ........................... | 422/100 |
| 2008/0242556 A1 | 10/2008 | Cao et al. | |
| 2010/0066348 A1 | 3/2010 | Merz et al. | |
| 2011/0227558 A1 | 9/2011 | Mannion et al. | |
| 2011/0279125 A1 | 11/2011 | Bedell et al. | |
| 2011/0308949 A1 | 12/2011 | Afzali-Azdakani et al. | |

OTHER PUBLICATIONS

H. Cao, et al., "Fabrication of 10 nm Enclosed Nanofluidic Channels," Applied Physics Letters, vol. 81., No. 1., 2002, pp. 174-176.
R. Fan, et al., "DNA Translocation in Inorganic Nanotubes," Nano Letters, vol. 5., No. 9, 2005, pp. 1633-1637.
M. Gracheva, et al., "p-n. Semiconductor Membrane for Electrically Tunable Ion Current Rectification and Filtering," Nano Letters, vol. 7, No. 6, 2007; pp. 1717-1722.
W. Guan, et al., "Field-Effect Reconfigurable Nanofluidic Ionic Diodes," Nature Communications, vol. 2., 2011, 506; 8 pages.
Y. He, et al., "Controlling DNA Translocation Through Gate Modulation of Nanopore Wall Surface Charges," ACS Nano, vol. 5, No. 7, 2011; pp. 5509-5518.
Y. He, et al., "Gate Manipulation of DNA Capture into Nanopores," ACE Nano, vol. 5., No. 10, 2011, pp. 8391-8397.

(Continued)

*Primary Examiner* — Tran Tran
(74) *Attorney, Agent, or Firm* — Cantor Colburn LLP; Vazken Alexanian (57) ABSTRACT

A technique includes providing a nanodevice. A gate electrode structure has nanochannels with a first end connected to a first common trench and a second end connected to a second common trench. A gate electrode extends laterally as a continuous line on the gate electrode structure and is formed in each of the nanochannels. The gate electrode forms a separate nano-ring electrode around a partial circumference inside each of the nanochannels. The gate electrode is parallel to the first and second common trenches and is perpendicular to the nanochannels.

8 Claims, 10 Drawing Sheets

(56) References Cited

OTHER PUBLICATIONS

J. Heng, et al., "Stretching DNA Using the Electric Field in a Synthetic Nanopore," Nano Letters, vol. 5, No. 10, 2005; pp. 1883-1888.
R. Karnik, et al., "Electrostatic Control of Ions and Molecules in Nanofluidic Transistors," Nano Letters, vol. 5, No. 5., 2005; pp. 943-948.
S-W. Nam, et al., "Ionic Field Effect Transistors with sub-10 nm Multipke Nanopores," Nano Letters, vol. 9, No. 5, 2009; pp. 2044-2048.
S-W. Nam, et al., "Sub-10-nm Nanochannels by Self-Sealing and Self-Limiting Atomic Layer Deposition," Nano Letters, vol. 10, No. 9, 2010, pp. 3324-3329.

* cited by examiner

FIG. 5A Trapping: Pulling by Gate Voltage Bias

FIG. 5B Stretching: Pushing by Gate Voltage Bias

NANO-RING GATE ELECTRODE NANOCHANNELS

BACKGROUND

Embodiments relate to nanodevices, and more particularly to nano-ring gate electrodes formed in nanochannels.

Nanopore sequencing is a method for determining the order in which nucleotides occur on a strand of deoxyribonucleic acid (DNA). A nanopore is a small hole in the order of several nanometers in internal diameter. The theory behind nanopore sequencing relates to what occurs when the nanopore is immersed in a conducting fluid and an electric potential (voltage) is applied across the nanopore. Under these conditions, a slight electric current due to conduction of ions through the nanopore can be measured, and the amount of current is very sensitive to the size and shape of the nanopore. If single bases or strands of DNA pass (or part of the DNA molecule passes) through the nanopore, this can create a change in the magnitude of the current through the nanopore. Other electrical or optical sensors can also be placed around the nanopore so that DNA bases can be differentiated while the DNA passes through the nanopore.

DNA could be driven through the nanopore by using various methods. For example, an electric field might attract the DNA towards the nanopore, and DNA might eventually pass through the nanopore.

BRIEF SUMMARY

According to an embodiment, a nanodevice is provided. The nanodevice includes a gate electrode structure having nanochannels with a first end connected to a first common trench and a second end connected to a second common trench, and a gate electrode extended laterally as a continuous line on the gate electrode structure and formed in each of the nanochannels. The gate electrode forms a separate nano-ring electrode around a partial circumference inside each of the nanochannels. The gate electrode is parallel to the first and second common trenches and is perpendicular to the nanochannels.

According to an embodiment, a method of providing a nanodevice is provided. The method includes providing a gate electrode structure having nanochannels with a first end connected to a first common trench and a second end connected to a second common trench, and providing a gate electrode which extends laterally as a continuous line on the gate electrode structure and is formed in each of the nanochannels. The gate electrode forms a separate nano-ring electrode around a partial circumference inside each of the nanochannels. The gate electrode is parallel to the first and second common trenches and is perpendicular to the nanochannels.

According to an embodiment, a method of controlling biomolecules in a nanodevice is provided. The method includes providing a gate electrode structure having a nanochannel with a first end connected to a first common trench and a second end connected to a second common trench, and providing a gate electrode which extends laterally as a continuous line on the gate electrode structure and is formed in the nanochannel. The gate electrode forms a nano-ring electrode around a partial circumference inside of the nanochannel. The gate electrode is parallel to the first and second common trenches and is perpendicular to the nanochannel. A biomolecule is trapped in the nanochannel by applying a first voltage to the gate electrode.

Other systems, methods, apparatus, design structures, and/or computer program products according to embodiments will be or become apparent to one with skill in the art upon review of the following drawings and detailed description. It is intended that all such additional systems, methods, apparatus, design structures, and/or computer program products be included within this description, be within the scope of the exemplary embodiments, and be protected by the accompanying claims. For a better understanding of the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features are apparent from the following detailed description taken in conjunction with the accompanying drawings in which:

DETAILED DESCRIPTION

Reliable and stable electrical-trap generation is important for manipulation of charged molecules in bio-electronic interface devices, such as an ionic transistor. To this point, a stable device performance of the ionic transistor has been hardly achieved because of drawbacks, such as leakage current or shorting current, when the nanodevice is immersed in a liquid solution. Direct exposure of gate-metal/gate-oxide surface to cis reservoir or trans reservoir has led to significant leakage and shorting problems, which hinders reliable electronic functions of the nanodevice, such as detection and manipulation of charged molecules.

Figure 1:
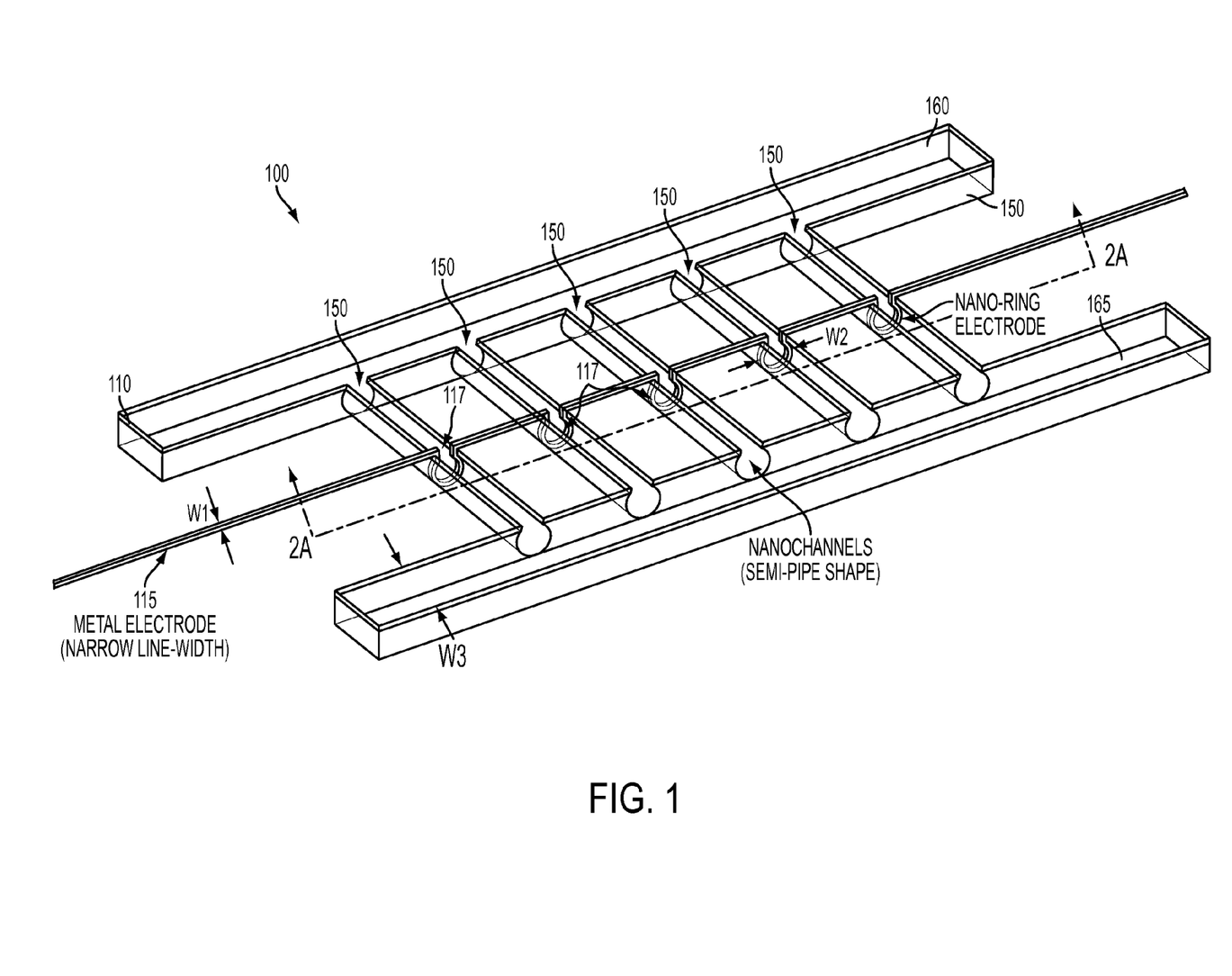
FIG. 1 illustrates a perspective view of a thin stripe-type gate electrode structure according to an embodiment.

FIG. 1 illustrates a perspective view of a thin stripe-type gate electrode structure 100 to create a highly-localized electrical potential trap coupling with a nanochannel structure according to an embodiment. FIG. 1 shows a translucent view of features in the thin stripe-type gate electrode structure 100 for explanation purposes.

The thin stripe-type gate electrode structure 100 is formed in a base material 105 with a hard mask 110 on top. Electron beam lithography is utilized to etch the sub-20 nm features of a single thin gate electrode 115 and narrow nanochannels 150. There may be 1-N nanochannels 150, where N is the last nanochannel. The nanochannels 150 each have one end connected to a first common trench 160 and the opposite end connected to a second common trench 165. The first and second common trenches 160 and 165 are etched into the base material 105.

Figure 2A:
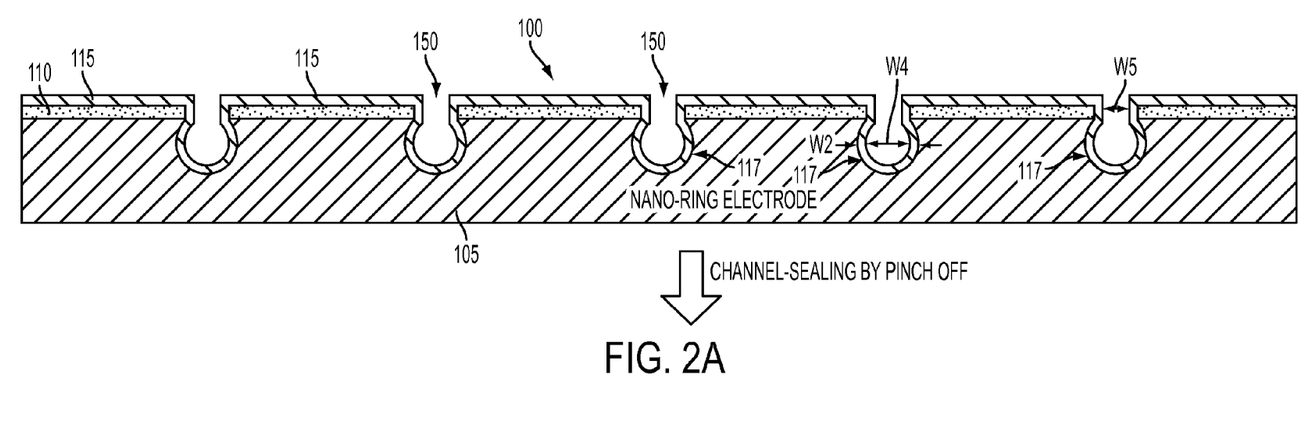
FIGS. 2A and 2B illustrate cross-sectional views of the nanochannel sealing process of the thin stripe-type gate electrode structure according to an embodiment.
Figure 2B:
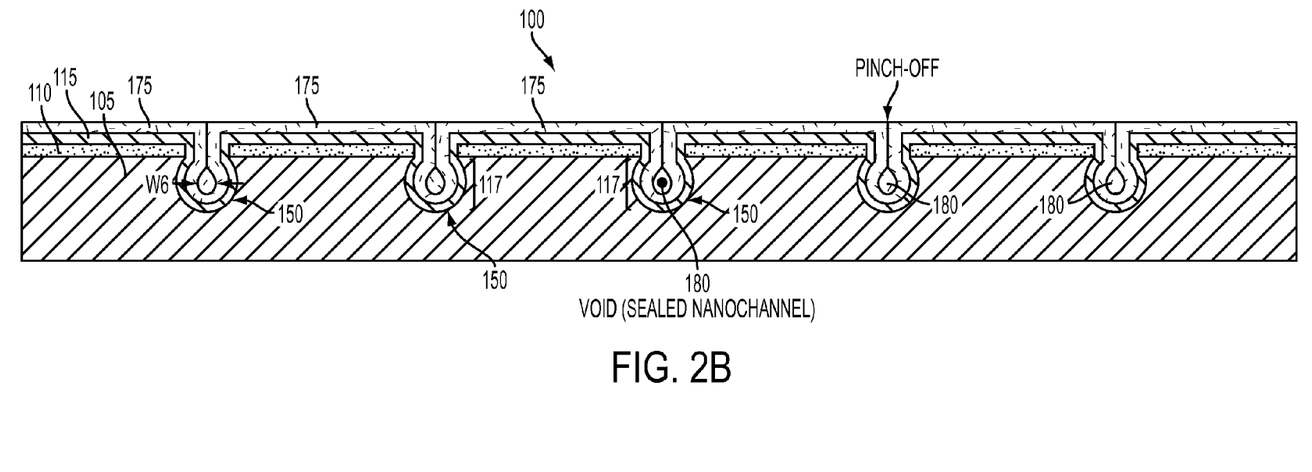

FIGS. 2A and 2B illustrate cross-sectional views of the nanochannel sealing process (i.e., pinch off) of the thin stripe-type gate electrode structure 100 according to an embodiment. FIG. 2A shows a cross-sectional view taken from A-A in FIG. 1.

In FIG. 2A, the hard mask 110 is on the base material 105 but does not cover the nanochannels 150. The single thin gate electrode 115 is deposited (e.g., by conformal deposition) on the hard mask 110 and in each of the nanochannels 150. In the nanochannels 150, the gate electrode 115 forms a nano-ring gate electrode 117. Each nanochannel 150 has its own nano-ring gate electrode 117 formed by depositing the metal for the gate electrode 115. The nano-ring gate electrode 117 is a ring shape (like a circle) that conforms to the inner shape of the nanochannel 150, and the nano-ring gate electrode 117 is open at the top such that the ring shape of metal is not completely closed.

FIG. 2B illustrates depositing a sealing film 175 (via a conformal deposition method) to cover the top of thin stripe-type gate electrode structure 100 and to seal the nanochannel 150. The conformal sealing film 175 seals the nanochannel 150 but leaves a void/opening 180 within the sealed nanochannel 150. The voids 180 extend the entire length of the nanochannels 150 and connect to the first and second common trenches 160 and 165. The voids 180 (in the sealed nanochannels 150) allow the biomolecules and electrolyte to flow from the first common trench 160 to the second common trench 165.

The width/diameter (w2) of the nanochannel 150 is about 70 to 100 nanometers (nm). The width (w3) of the first and second common trenches 160 and 165 is about ~1 (micrometer) μm. The width (w1) of the thin gate electrode 115 is less than 20 nanometers, and accordingly, the width of the nano-ring electrode 117 is less than 20 nanometers. In another case, the gate electrode 115 has a line width (w1) of about 10 to 20 nanometers, and accordingly, the line width of the nano-ring electrode 117 is about 10 to 20 nanometers. The line width of the thin gate electrode 115 is the same as the width of the nano-ring gate electrode 117 formed in the nanochannels 150.

After the single thin gate electrode 115 is deposited, the interior width (w4) in the nanochannel 150 is about 30 to 60 nm. The width (w5) of the opening 180 of the nanochannel 150 in FIG. 2A is about 20 to 40 nm. Therefore, the diameter/width (w6) of the void 180 in FIG. 2B is sub 20 nm. The diameter/width (w6) of the void 180 is defined as following: w6=w4−w5. Therefore, the size of w6 is the difference in width between w4 and w5.

The thickness of the hard mask 110 is about 10 to 20 nm. The thickness of the thin gate electrode 115 is about 10 to 20 nm. The base material 105 may be an available wet-etching material such as an oxide, dielectric, etc., with a high-κ (i.e., high dielectric constant). The hard mask 110 may be a wet-etching hard mask material such as silicon. The thin gate electrode 115 may be a metal such as copper (Cu), gold (Au), silver (Ag), aluminum (Al), ruthenium (Ru), cobalt (Co), nickel (Ni), palladium (Pd), platinum (Pt), titanium (Ti), tantalum (Ta), titanium nitride (TiN), tantalum nitride (TaN) and/or other alloys. In addition, the gate electrode 115 can be transparent conducting oxide (TCO) materials such as indium-tin-oxide (ITO), zinc oxide (ZnO) and/or other alloys. The thin gate electrode 115 may be deposited using a conformal film deposition method for metal layers.

As can be seen in FIGS. 1 and 2 (and FIGS. 3 and 6 below), the thin stripe-type gate electrode 115 is perpendicularly aligned with lateral-type nanochannels 150. The crossover gate electrode 115 produces a localized electrical-potential trap in the nanochannel 150, which is beneficial for electrical manipulations of charged biomolecules. The nanochannel trench-shape (of nanochannels 150) is generated by electron-beam lithography (EBL) and reactive ion etching (RIE) process. Isotropic wet-etching process produces the undercut-geometry with round-shaped pipe structure. Upon the undercut-structure, a conformal metal-film is deposited. A thin stripe-type gate electrode 115 is patterned by EBL and a wet-etching process. The metal stripe is crossing the nanochannel, thus enabling a crossover junction structure. The conformal dielectric-film is deposited for sealing the nanochannel. The nanochannels are surrounded by dielectric/oxide (sealing film 175) and metal layers (i.e., nano-ring gate electrode 117) Gate electrode 115 and nano-ring gate electrode 117 are physically the same materials.

Figure 3A:
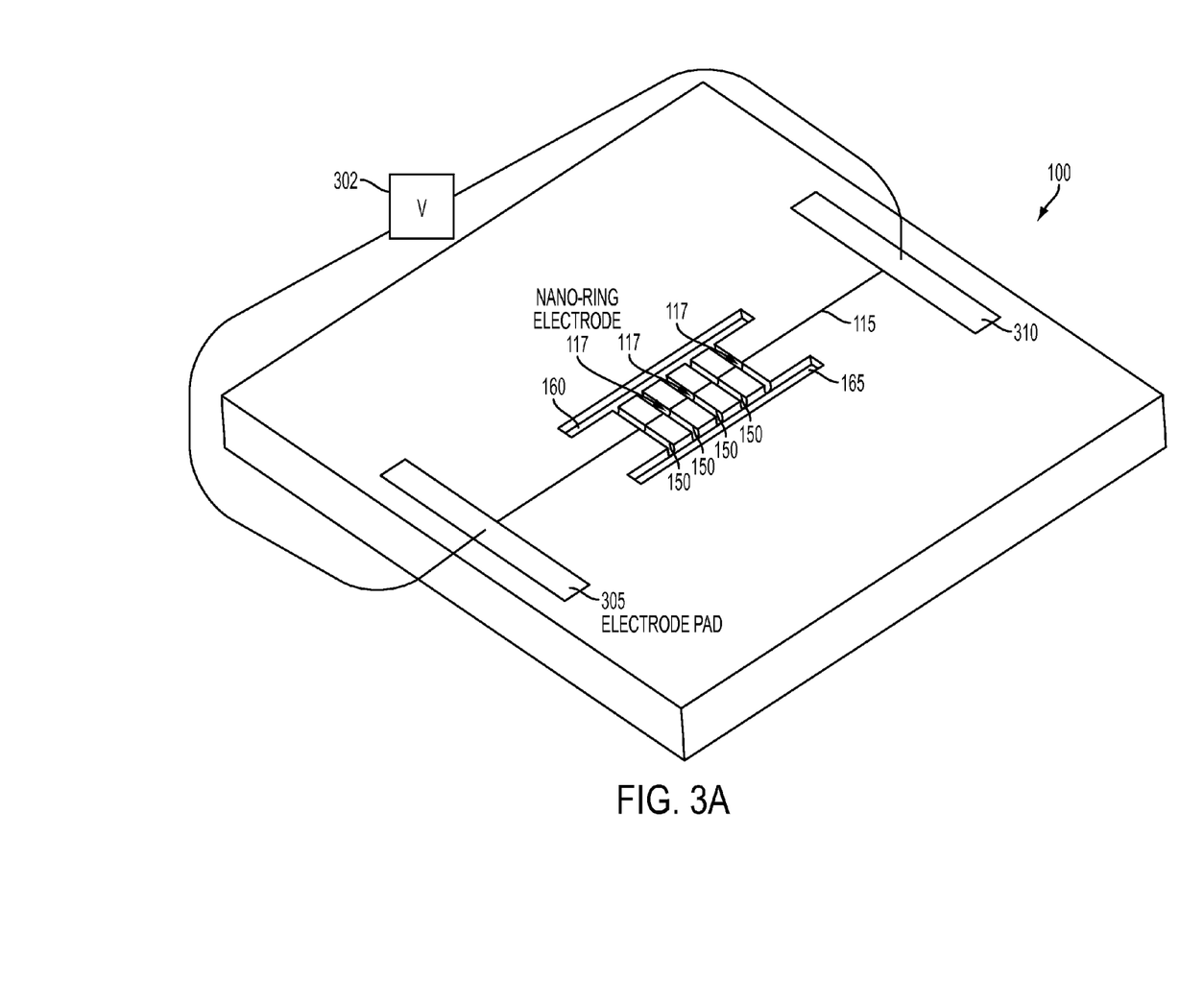
FIG. 3A illustrates the thin stripe-type gate electrode structure with metal electrode pads according to an embodiment.
Figure 3B:
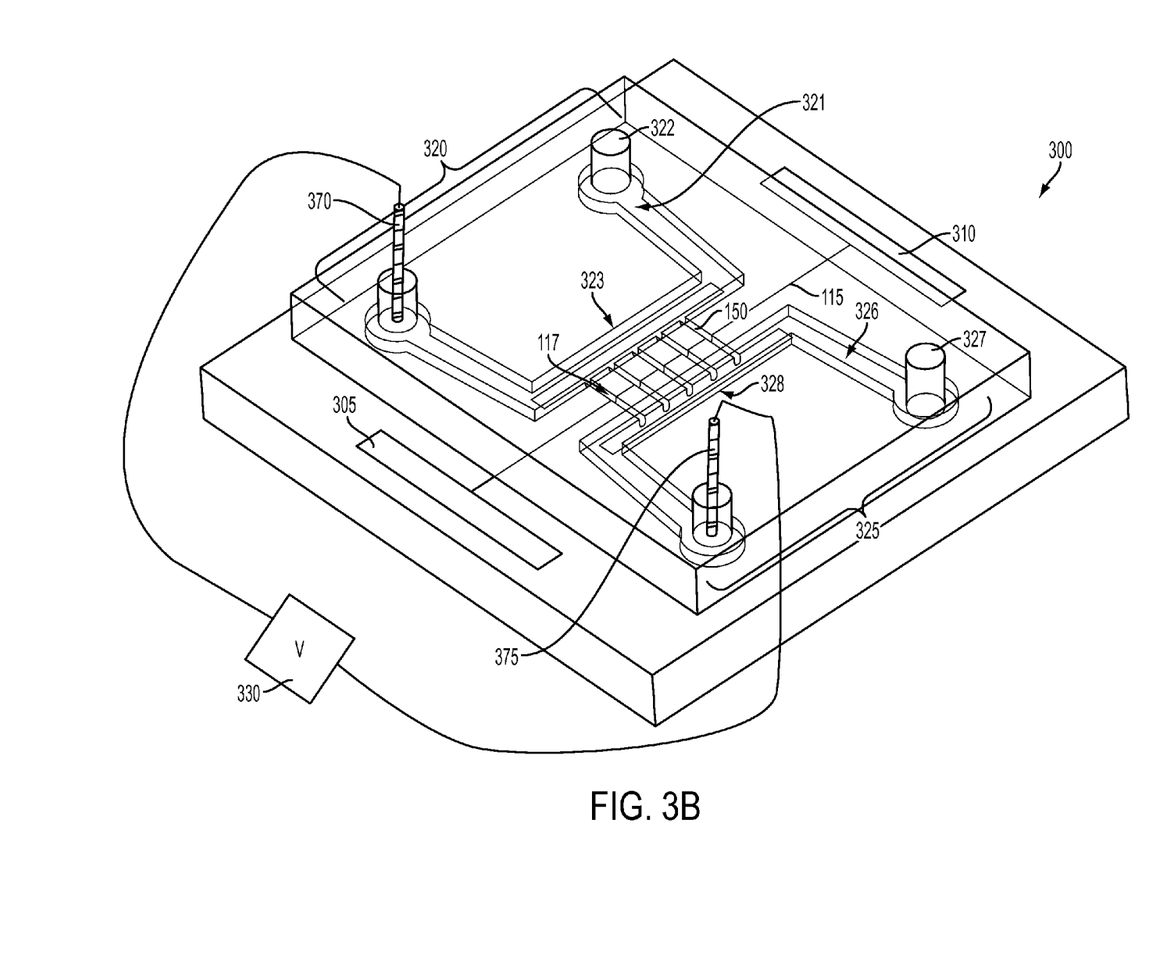
FIG. 3B illustrates a perspective view of a microchannel assembly formed on top of the thin stripe-type gate electrode structure in a nanodevice according to an embodiment.
Figure 3C:
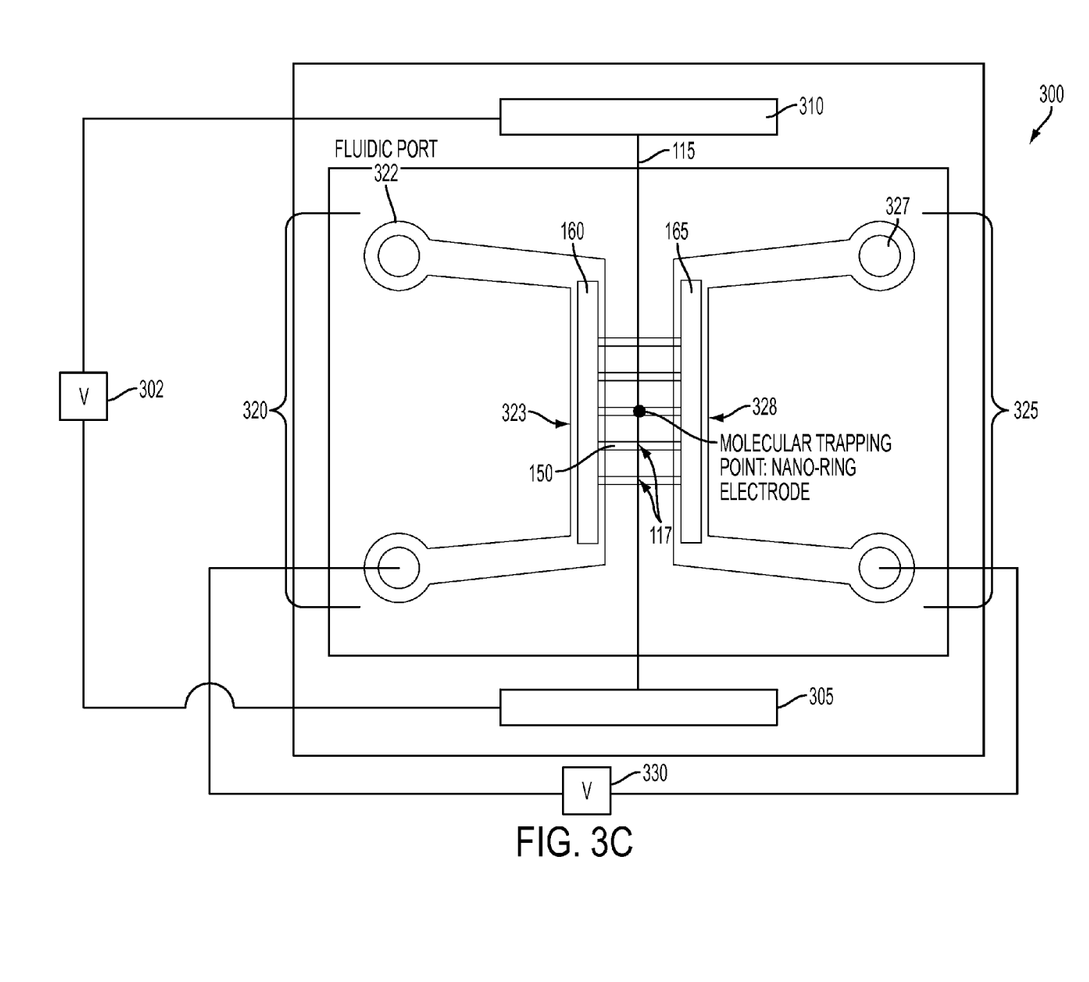
FIG. 3C illustrates a top down view of the nanodevice according to an embodiment.

FIGS. 3A, 3B, and 3C illustrate assembly of the thin stripe-type gate electrode structure 100 in a nanodevice 300 according to an embodiment. A microchannel (microfluidic) assembly is sealed to the electrode structure 100. FIGS. 3A, 3B, and 3C may be referred to generally as FIG. 3. Some details in FIGS. 1 and 2 are omitted or not identified in FIG. 3 so as not to obscure the FIG. 3, but it is understood that these elements are meant to be included.

FIG. 3A illustrates the thin stripe-type gate electrode structure 100 with first and second (metal) electrode pads 305 and 310 deposited at opposite ends of the single thin gate electrode 115. A conformal film deposition is used for metal layer deposition to deposit the single metal gate electrode 115. The metal line pattern of the single thin gate electrode 115 has a continuous line shape from one electrode pad 305 to the other electrode pad 310. Voltage of a voltage source 302 can be applied to trap a biomolecule in the nanochannel 150 when the voltage is applied with a polarity opposite the charge of the biomolecule.

FIG. 3B illustrates a perspective view of a microchannel assembly formed on top of and aligned with the thin stripe-type gate electrode structure 100 in a nanodevice 300 according to an embodiment. The microchannel assembly may be formed by existing microchannel fabrication as understood by one skilled in the art. The microchannel assembly (microfluidic chamber) is assembled with the ion transistor device (i.e., the structure 100 in FIG. 3A). Soft materials such as polydimethylsiloxane (PDMS) or organosilicon material can be used as microfluidic chamber materials. FIG. 3B shows a translucent view to illustrate certain internal details. Note that every detail of the thin stripe-type gate electrode structure 100 is not shown so as not to obscure the figure.

The microchannel assembly has a cis chamber 320 and trans chamber 325. The cis chamber 320 has an elongated portion 323 with an opening aligned to the first common trench 160, while the trans chamber 325 has an elongated portion 328 with an opening aligned to the second common trench 165. The cis chamber 320 includes two microchannels 321 connecting two ports 322 to the elongated portion 323. The trans chamber 325 includes two microchannels 326 connecting two ports 327 to the elongated portion 328.

An electrolyte solution fills the chambers 320 and 325 and the nanochannels 150. The electrolyte solution is a conductive fluid, such as a salt solution with ions for conducting electricity when voltage is applied. Biomolecules may be added to the cis chamber 320 via ports 322.

A voltage source 330 may be connected to the cis chamber 320 and the trans chamber 325 to drive biomolecules into and through the nanochannels 150 via cis electrode 370 and trans electrode 375.

FIG. 3C illustrates a top down view of the nanodevice 300 according to an embodiment. FIG. 3C shows a translucent view to illustrate certain internal details.

As can be seen in FIGS. 1-3 (along with FIG. 6 below), embodiments have a crossover type architecture between the nanochannels 150 and the (single) gate electrode 115, where the localized electrical-potential trap can be generated at the junction point of a 20 nm (w1) by 20 nm (w6) area (in one implementation gate electrode and nanochannel dimensions, respectively). In particular, conformal thin-film deposition methods are utilized, such as chemical vapor deposition (CVD) or atomic-layer deposition (ALD), to build the self-sealed nanochannel structure of the nanochannels 150. The thin stripe-type gate electrode 115 is perpendicularly aligned with the nanochannel 150, thus enabling crossover junction geometry. The surrounding gate electrode 115 (i.e., each separate nano-ring electrode 117 in each respective nanochannel 150) formed by conformal film-deposition is configured to provide a highly efficient gate coupling behavior of ionic transport. In addition, due to the separation of gate electrode geometry (of the nano-ring electrodes 117) from cis chamber 320 and/or trans chamber 325, the device-structure of the nanodevice 300 is free from leakage-current during ionic-transistor device operations.

Figure 4:
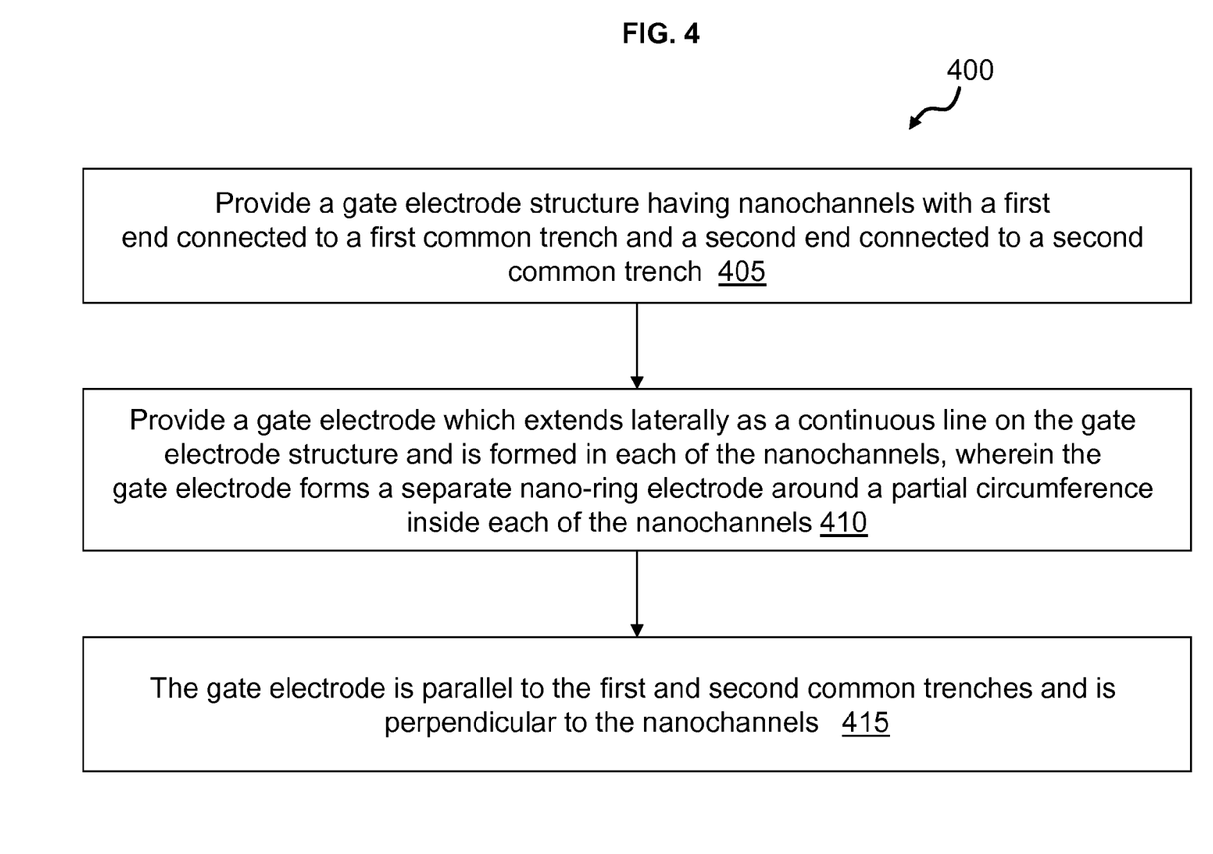
FIG. 4 illustrates a method of providing the nanodevice according to an embodiment.

Now turning to FIG. 4, a method 400 of providing the nanodevice 300 is illustrated according to an embodiment. Reference can be made to FIGS. 1-3. The gate electrode structure 100 is provided with nanochannels 150 having a first end connected to the first common trench 160 and a second end connected to a second common trench 165 at block 405.

At block 410, the gate electrode 115 extends laterally as a continuous (metal) line on the gate electrode structure 100 and is formed in each of the nanochannels 150, such that the gate electrode 115 forms separate nano-ring electrodes 117 around a partial circumference inside each of the nanochannels 150.

The gate electrode 115 is formed parallel to the first and second common trenches 160 and 165 and is formed perpendicular to the nanochannels 150 at block 415.

The gate electrode 115, extending as the continuous metal line, has a line width (w1) of less than 20 nanometers, and accordingly, the line width of the nano-ring electrode 117 is less than 20 nanometers. In another case, the gate electrode 115 extending as the continuous line has a line width (w1) of about 10 to 20 nanometers, and accordingly, the line width of the nano-ring electrode 117 is about 10 to 20 nanometers.

The nano-ring electrode 117 has a ring shape with an opening at the top of the ring shape.

The nanochannels 150 are each sealed by a conformal material within a circumference of the nano-ring electrode 117 to leave the void 180 in each of the nanochannels 150. The void 180 is an opening that extends from the first common trench 160 and to the second common trench 165, such that the electrolyte solution and biomolecules can traverse through the nanochannels 150.

The first electrode pad 305 connects to one end of the gate electrode 115 and the second electrode pad 310 connects to an opposite end of the gate electrode 115, such that the gate electrode 115 is in the continuous line between the first and second electrode pads 305 and 310.

A biomolecule is captured in the nano-ring electrode 117 at a cross point of the gate electrode 115 and a particular nanochannel 150.

Additionally, a biomolecule (e.g., negatively charged) may be trapped in the nanochannel 150 by applying a first voltage (e.g., +0.5 volts (V)) to the gate electrode 115 via the voltage source 302. In response to trapping the biomolecule, the biomolecule (DNA, RNA, protein, etc.) is stretched in the nanochannel 150 by applying a second voltage (e.g., −0.5 V) to the gate electrode 115 via the voltage source 302, where stretching the biomolecule is based on changing from the first voltage (+0.5 V) to the second voltage (−0.5) applied to the gate electrode 115. The first voltage is a different polarity from the second voltage, and the biomolecule has a charge, such that the biomolecule is either negatively charged or positively charged. The first voltage (e.g., +0.5 V) is applied with a first polarity that is opposite the charge on the biomolecule (e.g., negatively charged).

Applying the first voltage with the first polarity opposite the charge on the biomolecule pulls the biomolecule down to the region of the gate electrode 115 in the nanochannel 150. The second voltage (e.g., −0.5 V) is applied with a second polarity that is a same as the charge on the biomolecule (e.g., negatively charged). Applying the second voltage with the second polarity the same as the charge on the biomolecule pulls a first coiled part of the biomolecule in one direction and a second coiled part in an opposite direction while a higher voltage/potential is applied by the voltage source 330 (via the cis chamber electrode 370 in the cis chamber 320 and via the trans chamber electrode 375 in the trans chamber 325). Pulling the biomolecule in two opposite directions causes a straightened part between the first and second coiled parts of the biomolecule.

Figure 5A:
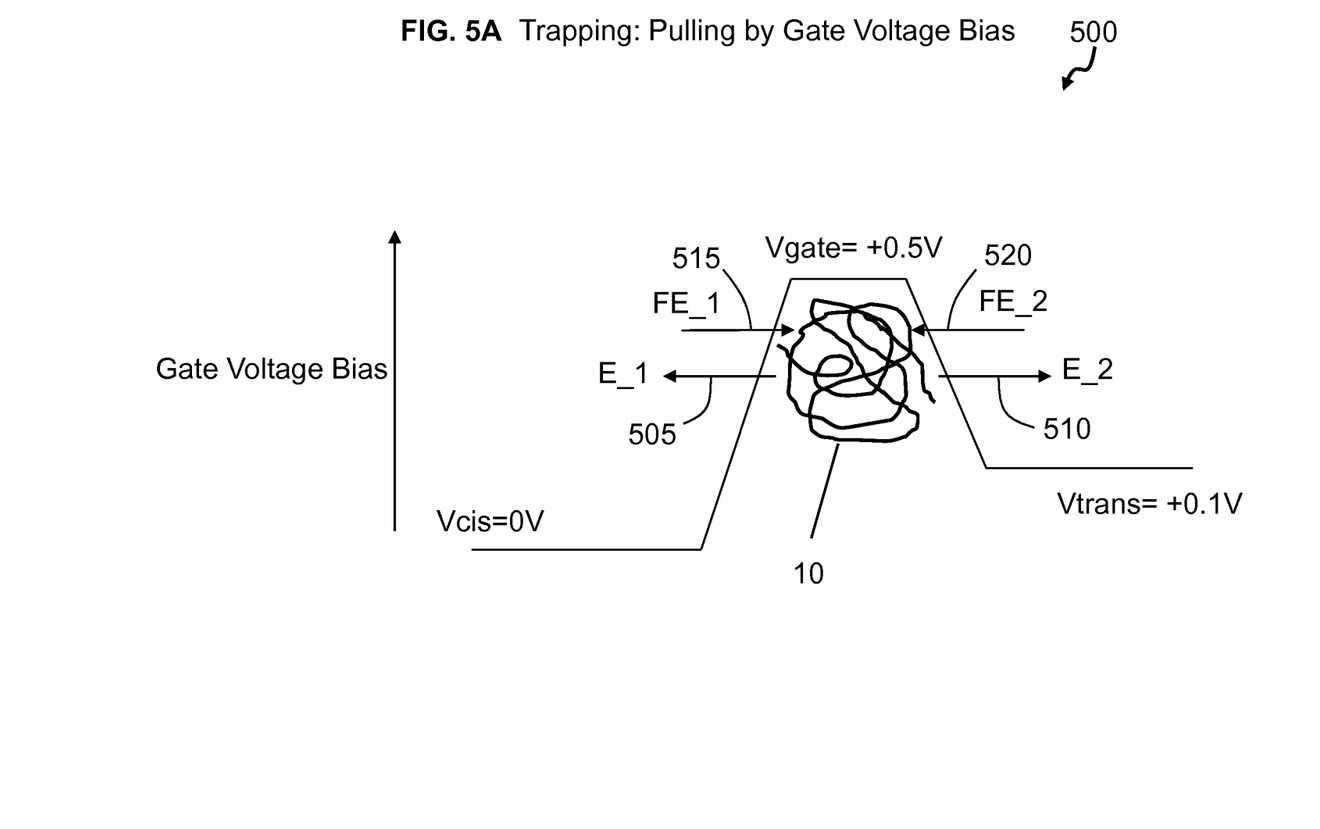
FIG. 5A is a voltage profile illustrating an example of trapping the biomolecule in the nanochannel using a single gate electrode according to an embodiment.
Figure 5B:
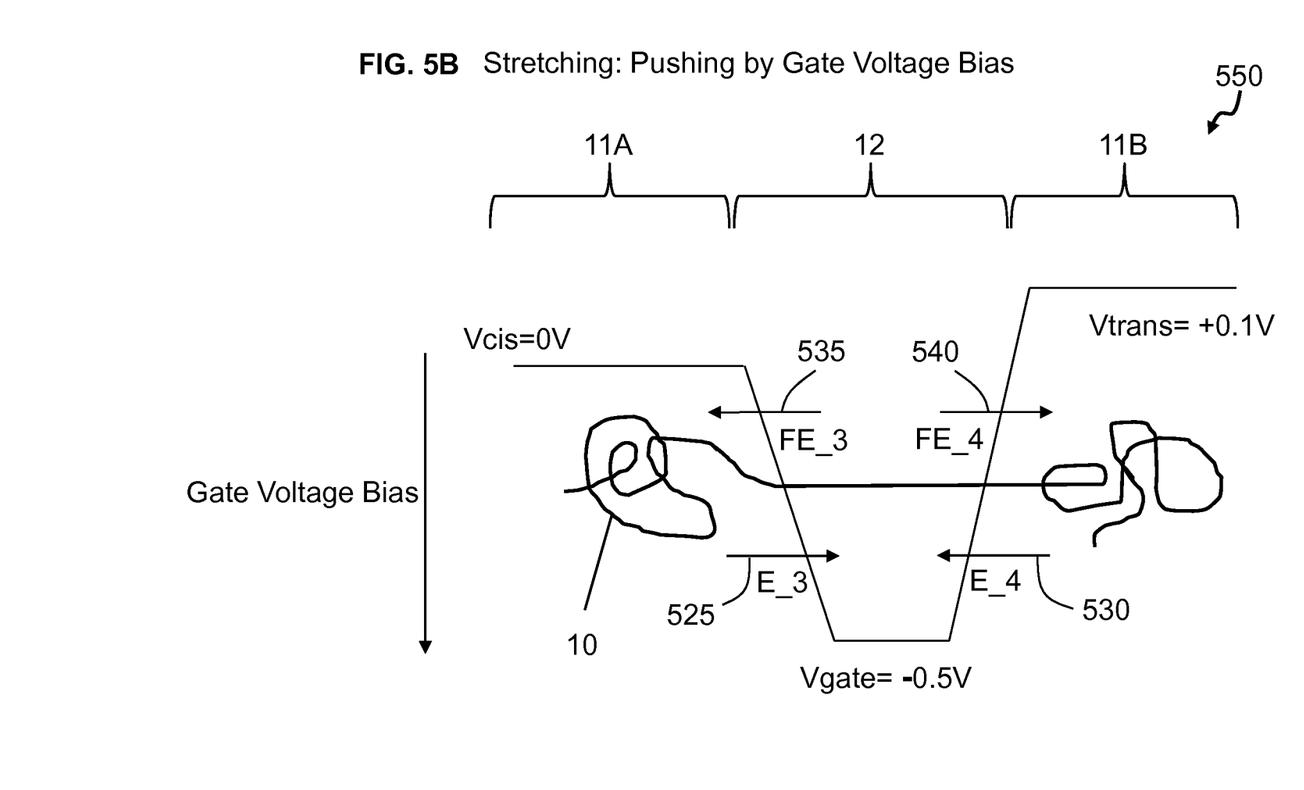
FIG. 5B is a voltage profile illustrating an example of stretching the biomolecule in the nanochannel using a single gate electrode according to an embodiment.

According to an embodiment, FIG. 5A is a voltage profile 500 illustrating an example of trapping the biomolecule 10 (e.g., DNA) in the nanochannel 150 of the nanodevice 300 using the single gate electrode 115 in the substrate 105. FIG. 5B is a voltage profile 550 illustrating stretching the biomolecule 10 in the nanochannel 150 of the nanodevice 300 using the single gate electrode 115 in the substrate 105 according to an embodiment. FIGS. 5A and 5B may generally be referred to as FIG. 5. Note that the details of the nanodevice 300 (shown/discussed in FIGS. 1-4) are omitted so as not to obscure FIG. 5, but it is contemplated that the elements in FIGS. 1-3 are meant to be included.

First, details of the trapping behavior are shown in FIG. 5A. A voltage is applied between electrodes 370 and 375 by voltage source 330, in order to drive the negatively charged biomolecule 10 into the nanochannel 150. Once in the nanochannel 150, a +0.5 V gate voltage (positive polarity) of the gate electrode 115 is turned on by voltage source 302. The positive polarity of the gate voltage traps the negatively charged biomolecule 10 in the nanochannel 150, by drawing/pulling the biomolecule 10 down to the gate electrode 115 and the substrate 105 (this may be referred to as the gate electrode region within the nanochannel 150). As a result of the +0.5 V gate voltage, two electric fields 505 (E_1) and 510 (E_2) in the nanochannel 150 create a trapping potential well for the negatively charged biomolecule 10. The electric fields 505 and 510 create forces 515 (FE_1) and 520 (FE_2) that hold the negatively charged biomolecule 10 in place within the nanochannel 150.

Second, once trapped in place, details of the stretching are further shown in FIG. 5B. As applied by the voltage source 330, assume that the voltage ($V_{Cis}$) on electrode 370 is 0 volts (in the top/cis reservoir 320) and the voltage ($V_{Trans}$) on electrode 375 is 0.1 volts (in the bottom/trans reservoir 325).

Also, assume now that −0.5 volts are applied to the gate electrode 115 at this time. Accordingly, the gate voltage (−0.5 V) is less than the voltage on the electrode 370 (0 V) in the top reservoir 320 and less than the voltage on the electrode 375 (0.1 V) in the bottom reservoir 325. The negative voltage on the gate electrode 115 creates two electric fields 525 (E_3) and 530 (E_4) in the nanochannel 150. The electric field 525 (E_3) points from the 0 V on the electrode 370 in the top reservoir 320 to the −0.5 V gate voltage of the gate electrode 115. The electric field 530 (E_4) points from the 0.1 V on the electrode 375 in the bottom reservoir 325 to the −0.5 V gate voltage of the gate electrode.

The electric field 525 creates a force 535 (FE_3) that pushes the biomolecule 10 to the left, whereas the electric field 530 (E_4) creates a force 540 (FE_4) that pushes the biomolecule 10 to the right. The repulsing forces 535 and 540 stretch the biomolecule 10, as shown in FIG. 5B. Viewed from left to right, the negatively charged biomolecule 10 has coiled part 11A, followed by stretched/straightened part 12, and then followed by coiled part 11B, all of which is a result of the forces 535 and 540.

Figure 6:
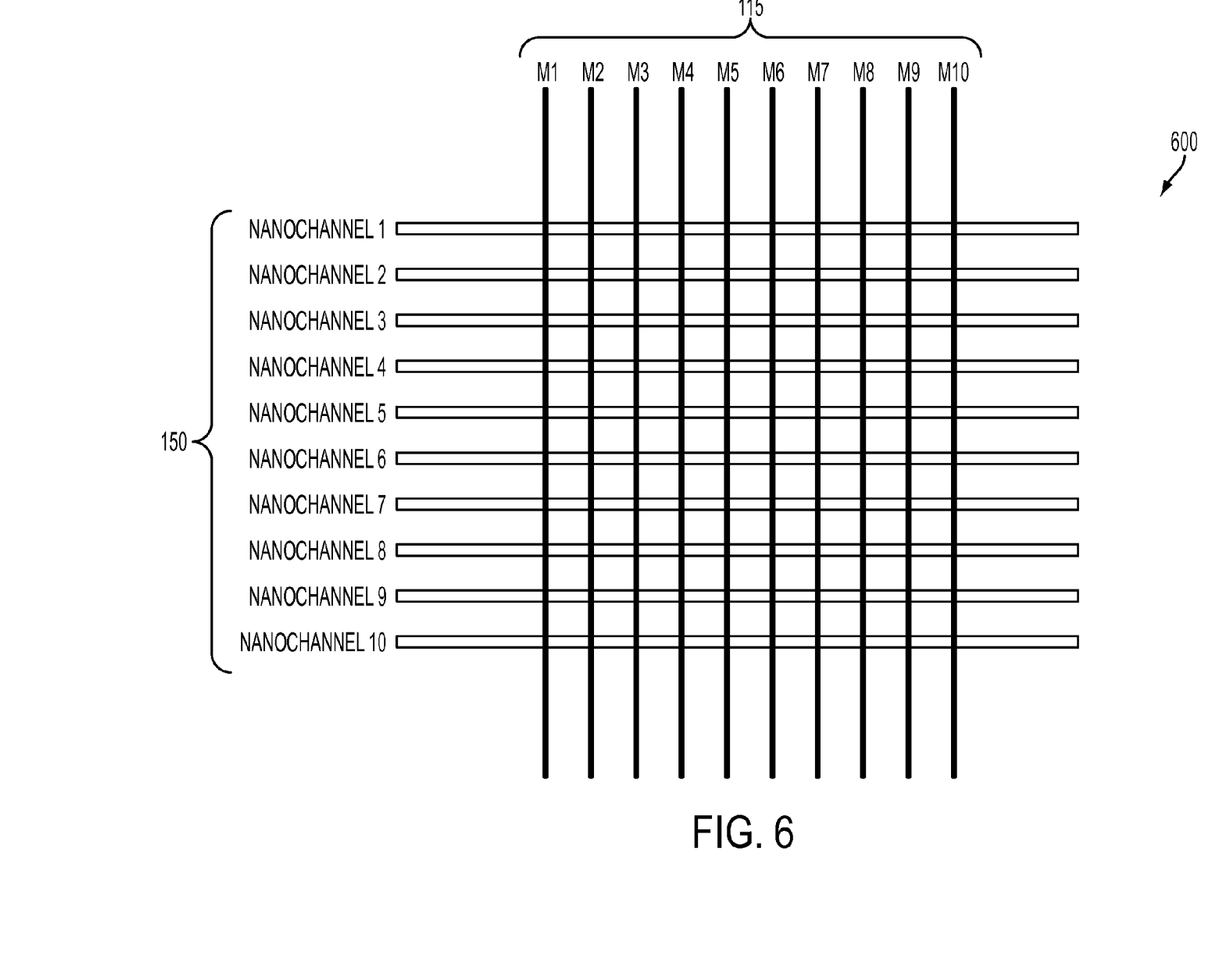
FIG. 6 illustrates a schematic of the nanodevice with multiple thin gate electrodes each crossing the narrow nanochannels according to an embodiment.

FIG. 6 illustrates a schematic 600 of the nanodevice 300 with multiple thin gate electrodes 115 each crossing the narrow nanochannels 150 according to an embodiment. Each location (e.g., at the nano-ring gate electrode 117) at which a gate electrode 115 crosses one of the narrow nanochannels 150 is a crosspoint. Each of the details in FIGS. 1-4 is meant to be included but some details are omitted for the sake of clarity.

The multiple thin gate electrodes 115 provide random access trapping that allows for addressing and trapping the biomolecules by the multiple metal electrodes M1-M10. When the opposite polarity (to the biomolecules in the nanochannel 150) is applied by the voltage source 302 to the multiple thin gate electrodes 115, this gives the multiple thin gate electrodes 115 more opportunities to trap (and then stretch) the biomolecules that are in the nanochannels 150. However, only a single gate electrode 115 is needed to trap the biomolecule is this one-electrode trapping system. Having the multiple metal electrodes M1-M10 does not mean that more than one gate electrode 115 is required to trap the biomolecule but provides a greater probability for of any one of the multiple metal electrodes M1-M10 to trap a biomolecule within a particular nanochannel 150.

Some technical benefits as discussed herein include the gate-electrode geometry, which has the thin stripe-type gate electrode structure (e.g., about or less than 20 nm line width. The gate electrode structure creates a highly-localized electrical-potential trap in the nanochannel. The nanodevice can contain multiple thin stripe gate electrodes in parallel. Also, the nanodevice provides a leakage-free device-performance in the lateral-type nanochannel ion transistor.

Figure 7:
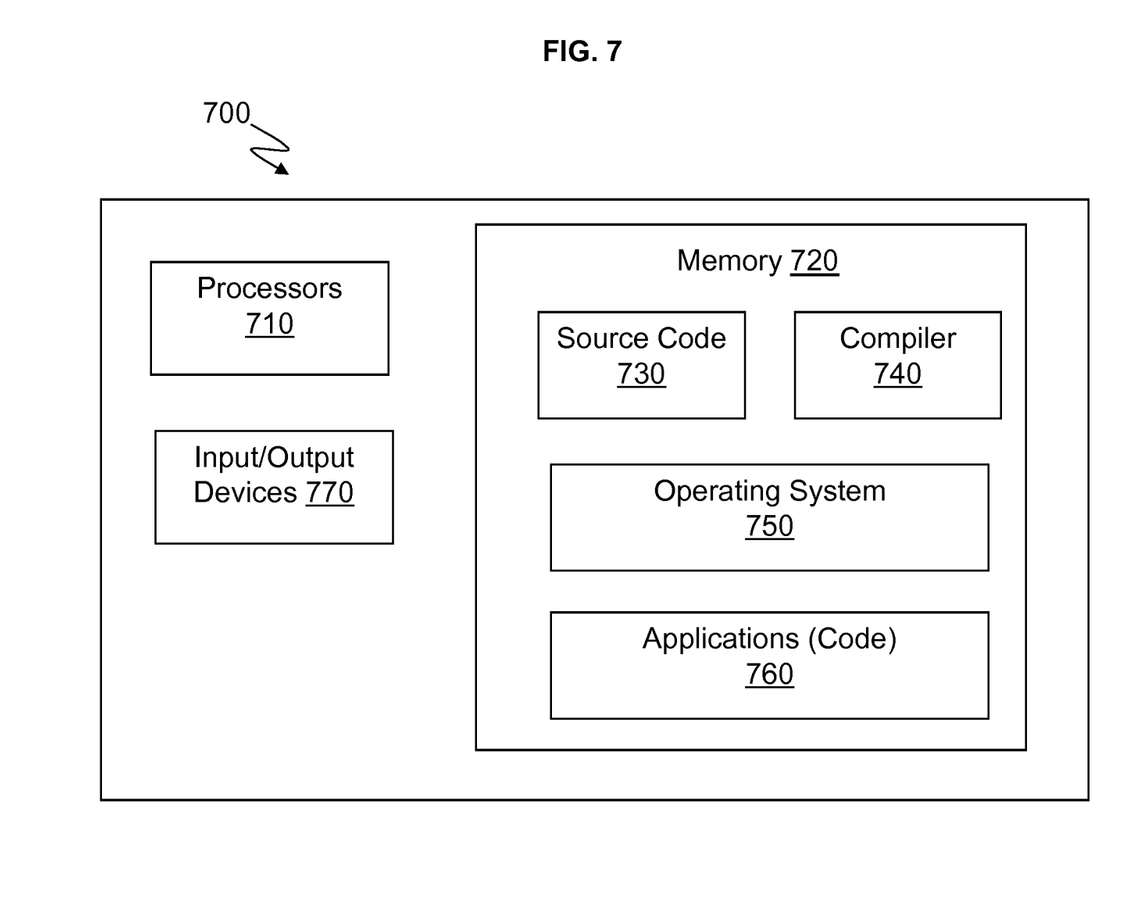
FIG. 7 illustrates a computer test setup which may implement, control, and/or regulate features discussed herein according to an embodiment.

FIG. 7 illustrates an example of a computer 700 (e.g., as part of the computer test setup for testing and analysis) which may implement, control, and/or regulate the respective voltages of the voltage sources, respective measurements of ammeters, and display screens for displaying various current amplitude as would be understood to one skilled in the art.

Various methods, procedures, modules, flow diagrams, tools, applications, circuits, elements, and techniques discussed herein may also incorporate and/or utilize the capabilities of the computer 700. Moreover, capabilities of the computer 700 may be utilized to implement features of exemplary embodiments discussed herein. One or more of the capabilities of the computer 700 may be utilized to implement, to connect to, and/or to support any element discussed herein (as understood by one skilled in the art. For example, the computer 700 which may be any type of computing device and/or test equipment (including ammeters, voltage sources, current meters, connectors, etc.). Input/output device 770 (having proper software and hardware) of computer 700 may include and/or be coupled to the nanodevices and structures discussed herein via cables, plugs, wires, electrodes, patch clamps, pads, etc. Also, the communication interface of the input/output devices 770 comprises hardware and software for communicating with, operatively connecting to, reading, and/or controlling voltage sources, ammeters, and current traces (e.g., magnitude and time duration of current), etc., as understood by one skilled in the art. The user interfaces of the input/output device 770 may include, e.g., a track ball, mouse, pointing device, keyboard, touch screen, etc., for interacting with the computer 700, such as inputting information, making selections, independently controlling different voltages sources, and/or displaying, viewing and recording current traces for each base, molecule, biomolecules, etc.

Generally, in terms of hardware architecture, the computer 700 may include one or more processors 710, computer readable storage memory 720, and one or more input and/or output (I/O) devices 770 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

The processor 710 is a hardware device for executing software that can be stored in the memory 720. The processor 710 can be virtually any custom made or commercially available processor, a central processing unit (CPU), a data signal processor (DSP), or an auxiliary processor among several processors associated with the computer 700, and the processor 710 may be a semiconductor based microprocessor (in the form of a microchip) or a macroprocessor.

The computer readable memory 720 can include any one or combination of volatile memory elements (e.g., random access memory (RAM), such as dynamic random access memory (DRAM), static random access memory (SRAM), etc.) and nonvolatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory 720 may incorporate electronic, magnetic, optical, and/or other types of storage media. Note that the memory 720 can have a distributed architecture, where various components are situated remote from one another, but can be accessed by the processor 710.

The software in the computer readable memory 720 may include one or more separate programs, each of which comprises an ordered listing of executable instructions for implementing logical functions. The software in the memory 720 includes a suitable operating system (0/S) 750, compiler 740, source code 730, and one or more applications 760 of the exemplary embodiments. As illustrated, the application 760 comprises numerous functional components for implementing the features, processes, methods, functions, and operations of the exemplary embodiments.

The operating system 750 may control the execution of other computer programs, and provides scheduling, input-output control, file and data management, memory management, and communication control and related services.

The application 760 may be a source program, executable program (object code), script, or any other entity comprising a set of instructions to be performed. When a source program, then the program is usually translated via a compiler (such as the compiler 740), assembler, interpreter, or the like, which may or may not be included within the memory 720, so as to operate properly in connection with the O/S 750. Furthermore, the application 760 can be written as (a) an object oriented programming language, which has classes of data and methods, or (b) a procedure programming language, which has routines, subroutines, and/or functions.

The I/O devices 770 may include input devices (or peripherals) such as, for example but not limited to, a mouse, keyboard, scanner, microphone, camera, etc. Furthermore, the I/O devices 770 may also include output devices (or peripherals), for example but not limited to, a printer, display, etc. Finally, the I/O devices 770 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 770 also include components for communicating over various networks, such as the Internet or an intranet. The I/O devices 770 may be connected to and/or communicate with the processor 710 utilizing Bluetooth connections and cables (via, e.g., Universal Serial Bus (USB) ports, serial ports, parallel ports, FireWire, HDMI (High-Definition Multimedia Interface), etc.).

In exemplary embodiments, where the application 760 is implemented in hardware, the application 760 can be implemented with any one or a combination of the following technologies, which are each well known in the art: a discrete logic circuit(s) having logic gates for implementing logic functions upon data signals, an application specific integrated circuit (ASIC) having appropriate combinational logic gates, a programmable gate array(s) (PGA), a field programmable gate array (FPGA), etc.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++, Labview software or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described herein with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one ore more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While the exemplary embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A nanodevice, the nanodevice comprising:
    a gate electrode structure having nanochannels with a first end connected to a first common trench and a second end connected to a second common trench; and
    a gate electrode extended laterally as a continuous line on the gate electrode structure and formed in each of the nanochannels, wherein the gate electrode forms a separate nano-ring electrode around a partial circumference inside each of the nanochannels;
    wherein the gate electrode is parallel to the first and second common trenches and is perpendicular to the nanochannels.

2. The nanodevice of claim 1, wherein the gate electrode extending as the continuous line has a line width of less than 20 nanometers.

3. The nanodevice of claim 1, wherein the gate electrode extending as the continuous line has a line width of about 10 to 20 nanometers.

4. The nanodevice of claim 1, wherein a line width of the nano-ring electrode is less than 20 nanometers.

5. The nanodevice of claim 1, wherein the nano-ring electrode has a ring shape with an opening at a top of the ring shape.

6. The nanodevice of claim 1, wherein the nanochannels are each sealed by a conformal material within a circumference of the nano-ring electrode to leave a void in each of the nanochannels; and
    wherein the void is an opening that extends from the first common trench and to the second common trench.

7. The nanodevice of claim 1, wherein a first electrode pad connects to one end of the gate electrode and a second electrode pad connects to an opposite end of the gate electrode, such that the gate electrode is in the continuous line between the first and second electrode pads.

8. The nanodevice of claim 1, wherein a biomolecule is captured in the nano-ring electrode at a cross point of the gate electrode and a nanochannel.

* * * * *